(12) United States Patent
Goto et al.

(10) Patent No.: US 6,174,827 B1
(45) Date of Patent: Jan. 16, 2001

(54) GLASS-CERAMIC SUBSTRATE FOR AN INFORMATION STORAGE MEDIUM

(75) Inventors: Naoyuki Goto; Junko Ishioka; Yasuyuki Kawashima, all of Sagamihara (JP)

(73) Assignee: Kabushiki Kaisha Ohara (JP)

( * ) Notice: Under 35 U.S.C. 154(b), the term of this patent shall be extended for 0 days.

(21) Appl. No.: 09/267,743

(22) Filed: Mar. 15, 1999

(30) Foreign Application Priority Data

| Mar. 23, 1998 | (JP) | 10-094020 |
| Apr. 20, 1998 | (JP) | 10-125316 |
| Dec. 10, 1998 | (JP) | 10-351682 |

(51) Int. Cl.$^7$ ............... C03C 10/04; C03C 10/14
(52) U.S. Cl. ............... 501/4; 501/5; 65/33.8; 65/61; 428/694 ST; 428/694 SG
(58) Field of Search ............... 501/4, 5; 65/33.8, 65/61; 428/694 ST, 694 SG (56) References Cited

U.S. PATENT DOCUMENTS

| 5,391,522 | * | 2/1995 | Goto et al. | 501/4 |
| 5,561,089 | * | 10/1996 | Ishizaki et al. | 501/10 |
| 5,567,217 | * | 10/1996 | Goto et al. | 501/5 |
| 5,580,363 | | 12/1996 | Goto et al. | 501/4 |
| 5,626,935 | | 5/1997 | Goto et al. | 428/64.1 |
| 5,744,208 | * | 4/1998 | Beall et al. | 501/5 |
| 5,866,489 | * | 2/1999 | Yamaguchi et al. | 501/4 |
| 5,985,777 | * | 11/1999 | Yamaguchi et al. | 501/4 |
| 6,034,011 | * | 3/2000 | Yamaguchi et al. | 501/4 |

FOREIGN PATENT DOCUMENTS

| 0779612 | 6/1997 | (EP) . |
| 0788093 | 8/1997 | (EP) . |
| 0810586 | 12/1997 | (EP) . |
| 0875886 | 11/1998 | (EP) . |

OTHER PUBLICATIONS

Patents Abstracts of Japan, vol. 097, No. 006, Jun. 30, 1997.
Patents Abstracts of Japan, vol. 011, No. 268, Aug. 29, 1987.

* cited by examiner

*Primary Examiner*—Karl Group
(74) *Attorney, Agent, or Firm*—Hedman, Gibson & Costigan, P.C.

(57) ABSTRACT

A glass-ceramic substrate for an information storage medium includes, as a predominant crystal phase, lithium disilicate ($Li_2O \cdot 2SiO_2$) or a combination of lithium disilicate and at least one crystal phase selected from the group consisting of α-quartz (α-$SiO_2$), α-quartz solid solution (α-$SiO_2$ solid solution), α-cristobalite (α-$SiO_2$) and α-cristobalite solid solution (α-$SiO_2$ solid solution). This substrate has Young's modulus (GPa)/specific gravity of 37 or over, surface roughness Ra (arithmetic mean roughness) of 5.0 Å or below, a coefficient of thermal expansion within a temperature range from −50° C. to +70° C. which ranges from $+65 \times 10^{-7}$/° C. to $+130 \times 10^{-7}$/° C. and bending strength of 400 MPa or over.

15 Claims, 3 Drawing Sheets

GLASS-CERAMIC SUBSTRATE FOR AN INFORMATION STORAGE MEDIUM

BACKGROUND OF THE INVENTION

This invention relates to a glass-ceramic substrate for an information storage medium and, more particularly, to a glass-ceramic substrate for an information storage medium such as a magnetic disk made of a glass-ceramic having improved super flatness of a surface of the substrate suitable for use in the near contact recording system or the contact recording system, a high Young's modulus and a low specific gravity capable of coping properly with a high-speed rotation, excellent mechanical properties, and a range of coefficient of thermal expansion matching with coefficients of thermal expansion of constituent elements of a drive device for the information storage medium. The invention relates also to a method for manufacturing the same and also to an information storage medium using this glass-ceramic substrate. In this specification, the term "information storage medium" means an information storage medium in the form of a disk and includes fixed type hard disks, removable type hard disks and card type hard disks used respectively for so-called "hard disks" for personal computers and storage of information in a network and other information storage medium in the form of a disk which can be used for storage of data in, e.g., digital video cameras and digital cameras.

Recent development of personal computers for multimedia purposes and digital video cameras and digital cameras which requires handling of a large amount of data has increased a demand for an information storage device of a higher recording capacity. As a result, for increasing the recording density, it is necessary in an information storage medium to increase its bit and track density and reduce the size of a bit cell. In conformity with the reduction in the size of the bit cell, a magnetic head performs its operation in closer proximity to the surface of a disk. As the magnetic head performs its operation in a near-contact state or contact state against the disk surface, it becomes important that a substrate has a super flat surface.

For satisfying this requirement, aside from the conventional landing zone system, development of a ramp loading system is under way according to which a magnetic head is completely in contact with the surface of a medium except for starting and stopping of the magnetic head when the magnetic head is moved away from the surface of the medium. Accordingly, a current requirement for a substrate for a magnetic information storage medium is a smoother surface.

For coping with the increase in the amount of information to be stored, a technical development is under way for a higher speed transfer of information by a higher speed rotation of a magnetic information storage medium used for a magnetic information storage device. As the number of revolution of a medium increases, deflection and deformation of the medium occur and this gives rises to a requirement for a higher Young's modulus and a lower specific gravity. Further, in addition to the conventional fixed type hard disks, information storage media such as a removable type hard disks and card type hard disks have been proposed and put into practice and application of digital video cameras and digital cameras for various uses have been started. Further uses of the medium for mobiles are expanding and, accordingly, mechanical strength of the substrate has increased its importance.

Development for new uses of information storage media for mobiles (e.g., APS cameras, portable telephones, digital cameras, digital video cameras and card drive), desk top PC (hard disk drive), servers (hard disk drive) and new high recording density media (e.g., perpendicular magnetic recording storage medium, Island magnetic storage medium and semiconductor memory) have also been started and, therefore, higher properties will be required for substrates for these information storage media.

Known in the art of magnetic disk substrate materials is aluminum alloy. The aluminum alloy substrate, however, has projections or spot-like projections and depressions on the substrate surface during polishing due to various defects of the material and, therefore, is not sufficient as a substrate for a high recording density storage medium in flatness and smoothness. Besides, since aluminum alloy is a soft material and has a low Young's modulus and surface hardness, vibration of the substrate takes place during a high-speed rotation of the medium with resulting deformation of the medium. Difficulty also arises in making the information storage medium thinner. Further, damage of the medium by contact with a head is liable to occur. Thus, the aluminum alloy substrate cannot sufficiently cope with the requirements for a high-speed recording.

As materials for overcoming the above problems of the aluminum alloy substrate, known in the art are chemically tempered glasses such as alumino-silicate glass ($SiO_2$—$Al_2O_3$—$Na_2O$). These materials, however, have the following disadvantages: (1) Since polishing is made after the chemical tempering process, the chemically tempered layer is seriously instable in making the disk thinner. (2) Since the glass contains $Na_2O$ as an essential ingredient, the glass has the problem that the film forming characteristics of the medium is deteriorated and, for preventing diffusion of $Na_2O$, it becomes necessary to apply a barrier coating over the entire surface of the substrate. This prevents stable production of the product at a competitive cost.

Aside from the aluminum alloy substrate and chemically tempered glass substrate, known in the art are some glass-ceramic substrates. For example, the glass-ceramics of a $SiO_2$—$Li_2O$—$MgO$—$P_2O_5$ system disclosed in U.S. Pat. No. 5,626,935 containing lithium disilicate ($Li_2O \cdot 2SiO_2$) and α-quartz (α-$SiO_2$) as main crystal phases is an excellent material as a material textured over the entire surface in which, by controlling the grain diameter of globular crystal grains of α-quartz, the conventional mechanical texturing or chemical texturing can be omitted and the surface roughness after polishing (Ra) can be controlled within a range from 15 Å to 50 Å. A surface roughness Ra (arithmetic mean roughness) which is sought today, however, is 5.0 Å or below, preferably 3.0 Å or below, and more preferably 2.0 Å or below and this prior art glass-ceramic cannot sufficiently cope with the requirement for the low glide height necessitated by the rapidly increasing recording density which requires such extremely small surface roughness (Ra), Further, no discussion or suggestion has been made in the patent about crystal grain diameter degree of crystallization and mechanical strength including Young's modulus and specific gravity which will be described later in this specification.

Japanese Patent Application Laid-open Publication No. Hei 10-45426 discloses a $SiO_2$—$Li_2O$—$K_2O$—$MgO$—$ZnO$—$P_2O_5$—$Al_2O_3$ system glass-ceramic or a $SiO_2$—$Li_2O$—$K_2O$—$MgO$—$ZnO$—$P_2O_5$—$Al_2O_3$—$ZrO_2$ system glass-ceramic suitable for laser texturing which contains, as its predominant crystal phase or phases, at least one of lithium disilicate ($Li_2O \cdot 2SiO_2$), a mixed crystal of lithium disilicate and α-quartz (α-$SiO_2$), and a mixed crystal of lithium disilicate and α-cristobalite (α-$SiO_2$). Surface roughness Ra which is sought today, however, is 5.0 Å or below, preferably 3.0 Å or below, more preferably 2.0 Å or below as described above and the prior art glass-ceramic substrates cannot sufficiently cope with the requirement for a reduced glide height which is necessitated by the rapidly increasing recording density. Besides, no discussion has been made in the prior art publication as to crystal grain diameter, degree of crystallization, and mechanical strength including Young's modulus and specific gravity.

Japanese Patent Application Laid-open Publication No. Hei 9-35234 discloses a magnetic disk substrate made of a glass-ceramic of a $SiO_2$—$Al_2O_3$—$Li_2O$ system having predominant crystal phases of lithium disilicate ($Li_2O \cdot 2SiO_2$) and β-spodumene ($Li_2O \cdot Al_2O_3 \cdot 4SiO_2$). This glass-ceramic, however, contains, as its predominant crystal phase, β-spodumene which has a negative thermal expansion characteristic which causes the substrate to have a negative thermal expansion characteristic and, in this glass-ceramic, growth of $SiO_2$ crystals such as α-quartz (α-$SiO_2$) and α-cristobalite (α-$SiO_2$) which have a positive thermal expansion characteristic and thereby cause the substrate to have a positive thermal expansion characteristic is extremely restricted. The arithmetic mean surface roughness of this glass-ceramic after polishing is defined as 20 Å or below but the arithmetic mean surface roughness disclosed in examples is a rough one of 12 Å–17 Å which fails to reach the above described desired surface roughness and, therefore, this glass-ceramic cannot cope sufficiently with the requirement for the low glide height of a magnetic head. Besides, the material which grows a crystal having a negative thermal expansion characteristic as a predominant crystal phase apparently adversely affects the substrate in difference in the coefficient of thermal expansion with respect to component parts of a drive device. Further, since this glass-ceramic requires a high temperature of 820° C. to 920° C. for crystallization which prevents a large scale production of the product at a competitive cost. Furthermore, no discussion has been made in the publication as to mechanical strength including crystal grain diameter, degree of crystallization and mechanical strength.

International Publication WO97/01164 which includes the above described Japanese Patent Application Laid-open Publication No. Hei 9-35234 discloses a glass-ceramic for a magnetic disk in which temperature for crystallization is reduced (680° C.–770° C.). A sufficient improvement however cannot be achieved in this substrate. Besides, crystals grown in all examples disclosed are β-eucryptite ($Li_2O \cdot Al_2O_3 \cdot 2SiO_2$) which has a negative thermal expansion characteristic and this adversely affects difference in the coefficient of thermal expansion with respect to component parts of a drive device. Further, no discussion has been made in this publication as to crystal grain diameter, degree of crystallization and mechanical strength.

It is, therefore, an object of the invention to eliminate the above described disadvantages of the prior art and provide a glass-ceramic substrate for an information storage medium having a super flat surface characteristic capable of coping with recording at a low glide height or contact recording of a magnetic head necessitated by increase in the recording capacity of an information storage medium, having properties capable of coping with a high-speed rotation of the medium necessitated by increase in the information transfer speed, and having a high mechanical strength adapted for uses as an information storage medium for mobiles.

It is another object of the invention to provide a method for manufacturing the glass-ceramic substrate.

It is another object of the invention to provide an information storage medium employing this glass-ceramic substrate.

More specifically, requirements for the glass-ceramic substrate according to the invention are summarized as follows:

(1) As the recording density increases, it becomes necessary to reduce the size of the bit cell. As the bit cell is reduced, the magnetic head performs its operation in closer proximity to the surface of an information storage medium. In case the magnetic head performs its operation at such a low glide height (near contact state) or in contact with the surface of the medium, the substrate is required to have a super flat surface having a surface roughness Ra of 5.0 Å or below, preferably 3.0 Å or below, and more preferably 2.0 Å or below.

(2) As the substrate is required to have a super flat surface, crystal grains in the substrate are required, for standing a precision polishing which is conducted almost in the level of atoms, to be of a specific crystal type which has chemical durability and physical properties and to have crystal grain diameter, crystal shape and degree of crystallization which can sufficiently cope with the high precision polishing.

(3) As the recording density increases, the number of rotation of the medium must be increased. For coping with such high-speed rotation of the medium, a higher Young's modulus and a lower specific gravity of the substrate become important.

(4) As uses of an information storage medium are expanded and particularly uses for mobiles are developed, mechanical strength of the substrate becomes important.

(5) Since positioning between a magnetic head and an information storage medium requires a high precision, the substrate and component parts of a drive device for the medium must have a size of a high precision. Accordingly, difference in a coefficient of thermal expansion between the substrate and the component parts of the drive device should be minimized in accordance with environmental temperature at which the substrate is used.

SUMMARY OF THE INVENTION

Accumulated studies and experiments made by the inventors of the present invention for achieving the above described objects of the invention have resulted in the finding, which has led to the present invention, that a glass-ceramic which is obtained by heat treating within a limited range a $SiO_2$—$Li_2O$—$K_2O$—$MgO$—$ZnO$—$P_2O_5$—$Al_2O_3$—$ZrO_2$ system glass contains, as its predominant crystal phase or phases, lithium disilicate ($Li_2O \cdot 2SiO_2$) or a combination of lithium disilicate and at least one crystal phase selected from the group consisting of α-quartz (α-$SiO_2$), α-quartz solid solution (α-$SiO_2$ solid solution), α-cristobalite (α-$SiO_2$) and α-cristobalite solid solution (α-$SiO_2$ solid solution), has crystal grains of the predominant crystal phase or phases which are fine and substantially of a globular shape, has an excellent surface characteristic after polishing, has a coefficient of thermal expansion matching with coefficients of thermal expansion of component parts of a drive device, and has a high Young's modulus, a low specific gravity and high mechanical strength.

For achieving the above described object of the invention, there is provided a glass-ceramic substrate for an information storage medium comprising, as a predominant crystal phase, lithium disilicate ($Li_2O \cdot 2SiO_2$) having a crystal grain diameter (average) of 0.05 μm or below.

In one aspect of the invention, the glass-ceramic substrate has Young's modulus (GPa)/specific gravity of 37 or over.

In another aspect of the invention, the glass-ceramic substrate consists of a crystal phase or phases and an amorphous phase, has a crystal grain diameter (average) of 0.05 μm or below wherein Young's modulus (GPa)/specific gravity is 37 or over.

In another aspect of the invention, degree of crystallization of the lithium disilicate crystal phase is within a range from 3% to 20%.

In another aspect of the invention, the glass-ceramic substrate comprises further at least one crystal phase selected from the group consisting of α-quartz (α-$SiO_2$), and α-quartz solid solution (α-$SiO_2$ solid solution), degree of crystallization of the α-quartz (α-$SiO_2$) and the α-quartz solid solution (α-$SiO_2$ solid solution) being within a range from 5% to 25% and a crystal grain diameter thereof (average) being 0.10 μm or below.

In another aspect of the invention, the glass-ceramic substrate comprises further at least one crystal phase selected from the group consisting of α-cristobalite (α-$SiO_2$) and α-cristobalite solid solution (α-$SiO_2$ solid solution), degree of crystallization of the α-cristobalite (α-$SiO_2$) and the α-cristobalite solid solution (α-$SiO_2$ solid solution) being within a range from 2% to 10% and a crystal grain diameter thereof (average) being 0.10 μm or below.

In another aspect of the invention, the glass-ceramic substrate comprises, as predominant crystal phases, lithium disilicate ($Li_2O \cdot 2SiO_2$) and at least one crystal phase selected from the group consisting of α-quartz (α-$SiO_2$), α-quartz solid solution (α-$SiO_2$ solid solution), α-cristobalite (α-$SiO_2$) and α-cristobalite solid solution (α-$SiO_2$ solid solution).

In another aspect of the invention, crystal grains of the predominant crystal phase or phases are fine and substantially of a globular shape.

In another aspect of the invention, the glass-ceramic substrate is substantially free of $Na_2O$ and PbO.

In another aspect of the invention, the glass-ceramic substrate has a surface roughness Ra (arithmetic mean roughness) after polishing of 5.0 Å or below.

In another aspect of the invention, the glass-ceramic substrate has a coefficient of thermal expansion within a range from $+65 \times 1^{-7}/°$ C. to $+130 \times 10^{-7}/°$ C. in a temperature range from $-50°$ C. to $+70°$ C.

In another aspect of the invention, the glass-ceramic substrate has bending strength of 400 MPa or over.

In another aspect of the invention, the glass-ceramic substrate has a composition which consists in weight percent of:

| | |
|---|---|
| $SiO_2$ | 70–77% |
| $Li_2O$ | 8–12% |
| $K_2O$ | 1–3% |
| MgO | 0–2% |
| ZnO | 0–2% |
| $P_2O_5$ | 1.5–3% |
| $ZrO_2$ | 2–7% |
| $Al_2O_3$ | 3–9% |
| $Sb_2O_3 + As_2O_3$ | 0–2%. |

In another aspect of the invention, there is provided a method for manufacturing the glass-ceramic substrate for an information storage medium which comprises steps of heat treating a base glass for nucleation under a temperature within a range from 500° C. to 600° C. for one to seven hours and further heat treating the glass for crystallization under a temperature within a range from 700° C. to 780° C. for one to twelve hours and thereafter polishing the glass-ceramic to a surface roughness Ra (arithmetic mean roughness) of 5 Å or below.

In still another aspect of the invention, there is provided an information storage disk provided by forming a magnetic film and, if necessary, other layers including a Ni—P plating, an undercoat layer, a protective layer and a lubricating layer, on a glass-ceramic substrate as defined above.

BRIEF DESCRIPTION OF THE DRAWINGS

In the accompanying drawings.

DETAILED DESCRIPTION OF THE INVENTION

Reasons for limiting the predominant crystal phases, crystal grain diameter, degree of crystallization, Young's modulus, specific gravity, mechanical strength, coefficient of thermal expansion, surface characteristics, composition and conditions of heat treatment will now be described. The composition of the glass-ceramic is expressed on the basis of composition of oxides as in their base glass.

Description will be made first about predominant crystal phases and crystal grain diameter.

The glass-ceramic substrate for an information storage medium made according to the present invention comprises lithium disilicate ($Li_2O \cdot 2SiO_2$) as a predominant crystal phase having a crystal grain diameter (average) of 0.05 μm or below. By reducing the crystal grain diameter of lithium disilicate to an extremely small one of 0.05 μm or below, the substrate can be polished to a desired surface roughness and can thereby provide an excellent super flat surface. In addition, by this extremely small grain diameter, a substrate having an excellent mechanical property, particularly bending strength can be provided. By selecting lithium disilicate as a predominant crystal phase, a glass-ceramic substrate having excellent chemical durability and physical property can be provided.

The degree of crystallization of the lithium disilicate crystal phase should preferably be 3% or over in view of the fact that it is a predominant crystal phase. The degree of crystallization of this crystal phase should preferably be 20% or below because it will be easy to design a substrate having proper properties of the invention (i.e., coefficient of thermal expansion, Young's modulus, specific gravity and surface roughness) within this range of degree of crystallization.

The glass-ceramic substrate should preferably contain, as a predominant crystal phase in addition to lithium disilicate, at least one of α-quartz (α-$SiO_2$) and α-quartz solid solution (α-$SiO_2$ solid solution). By containing this crystal phase as an additional predominant crystal phase, bending strength can be increased and a coefficient of thermal expansion within a temperature range from $-50°$ C. to $+70$ can be set within a higher range. For realizing these effects, the degree of crystallization of this predominant crystal phase should preferably be 5% or over and, for easily designing the glass-ceramic to a substrate having properties of the invention (particularly coefficient of thermal expansion, specific gravity and surface roughness), the degree of crystallization should preferably be 25% or below. The crystal grain diameter (average) of the predominant crystal phase should preferably be 0.10 µm or below for polishing the substrate to a desired surface roughness and obtaining a substrate having an excellent super flatness and excellent mechanical strength, particularly bending strength.

The glass-ceramic substrate according to the invention should preferably contain, in addition to lithium disilicate, at least one of α-cristobalite (α-$SiO_2$) and α-cristobalite solid solution (α-$SiO_2$ solid solution) as a predominant crystal phase. By containing this additional predominant crystal phase, bending strength can be increased remarkably and a coefficient of thermal expansion within a temperature range from −50° C. to +70° C. can be set within a higher range. For realizing these effects, the degree of crystallization of the predominant crystal phase should preferably be 2% or over and, for easily designing the glass-ceramic to a substrate having properties of the invention (particularly surface roughness and coefficient of thermal expansion), the degree of crystallization should preferably be 10% or below. The crystal grain diameter (average) of the predominant crystal phase should preferably be 0.10 µm or below for polishing the substrate to a desired surface roughness and obtaining a substrate having an excellent super flatness and excellent mechanical strength, particularly bending strength.

In sum, the glass-ceramic substrate according to the invention should preferably contain, as a predominant crystal phase or phases, lithium disilicate ($Li_2O \cdot 2SiO_2$), or lithium disilicate and at least one crystal phases selected from the group consisting of α-quartz (α-$SiO_2$), α-quartz solid solution (α-$SiO_2$ solid solution), α-cristobalite (α-$SiO_2$) and α-cristobalite solid solution (α-$SiO_2$ solid solution). It has been found that the predominant crystal phase is an important factor which determines the surface characteristic which is influenced by a coefficient of thermal expansion, mechanical strength and shape of crystal grains and that, for realizing the properties required for a substrate coping with the high recording density, the above described crystal phase or phases must be contained as the predominant crystal phase or phases.

Description will now be made about the crystal grain diameter of the predominant crystal phases and the surface characteristics of the substrate.

As described previously, as the recording density of the information storage medium increases, the glide height of the magnetic head is extremely reduced to 0.025 µm or below and the near contact recording system or the contact recording system has been developed. For coping with such tendency, the medium must have a more flat surface than the prior art disks. If one attempts to perform high recording density inputting and outputting of information on a magnetic information storage medium having a surface of the prior art flatness, proper inputting and outputting of a magnetic signal cannot be achieved because distance between the magnetic head and the medium is too large. If this distance is reduced, collision of the magnetic head against the surface of the medium occurs with resulting damage to the head or medium. For preventing occurrence of damages to the head and medium notwithstanding the extremely low glide height or the contact recording, the surface roughness Ra (arithmetic mean roughness) of the substrate should preferably be 5.0 Å or below, more preferably 3.0 Å or below and, more preferably 2.0 Å or below.

For obtaining a glass-ceramic substrate having such flatness, the shape and diameter of grown crystal grains become important factors. For workability and surface roughness of the substrate, the grown crystal grains should preferably be fine globular grains.

The substrate for an information storage medium is required to be free from defects such as crystal anisotropy, foreign matters and impurities and have a uniform, homogeneous and fine texture. These requirements are fully satisfied by the substrate of the invention which contains the above described predominant crystal phase (lithium disilicate, or a combination of lithium disilicate and at least one of α-quartz, α-quartz solid solution, α-cristobalite and α-cristobalite solid solution) having the above described crystal grain diameter and crystal grain shape.

The glass-ceramic substrate having the above described predominant crystal phase or phases has a coefficient of thermal expansion as described below which is suited for a substrate for an information storage medium. The glass-ceramic substrate of the invention should preferably not contain, as a predominant crystal phase, β-spodumene, β-eucryptite, β-cristobalite (β-$SiO_2$) or β-quartz which has a negative thermal expansion characteristic.

Description will now be made about a coefficient of thermal expansion. As the recording density increases, positioning of the magnetic head relative to the information storage medium requires a high precision and, therefore, a high precision size is required for the substrate and respective component parts for the medium. Therefore, an influence of difference in the coefficient of thermal expansion between the substrate and the component parts for the medium cannot be ignored and difference in the coefficient of thermal expansion must be reduced to the maximum extent possible. More precisely, there is a case where it is preferable that a coefficient of thermal expansion of the substrate is only slightly larger than a coefficient of thermal expansion of the component parts of the drive device. As component parts for a small size magnetic information storage medium, ones having a coefficient of thermal expansion in a range from $+90 \times 10^{-7}$/° C. to $+100 \times 10^{-7}$/° C. are frequently used so that the substrate needs to have a coefficient of thermal expansion of the same order. There is a case, however, where a drive maker employs a component part made of a material which has a coefficient of thermal expansion which is out of the above described range, i.e., a coefficient of thermal expansion within a range from about $+70 \times 10^{-7}$/° C. to about $+125 \times 10^{-7}$/° C. For this reason, in the crystal system of the present invention, a range of coefficient of thermal expansion has been determined so that the substrate will be applicable to as wide a variety of materials of component parts as possible while having sufficient regard to the strength of the substrate. It has been found that the coefficient of thermal expansion should preferably be within a range from $+65 \times 10^{-7}$/° C. to $+130 \times 10^{-7}$/° C. within a temperature range from −50° C. to +70° C. A more preferable range of the coefficient of thermal expansion within the same temperature range is from $+95 \times 10^{-7}$/° C. to $+110 \times 10^{-7}$/° C.

Description will be made now about Young's modulus and specific gravity. For preventing deformation and vibration of the substrate in a high-speed rotation exceeding 10000 rpm coping with a high-speed transfer of information, the glass-ceramic substrate must have high rigidity and low specific gravity. Further, in the case where the medium is used for uses where a magnetic head in operation is in contact with the medium or where the medium is used for a portable type device such as a removable type storage device, the substrate material must also have sufficient mechanical strength, Young's modulus and surface hardness to be adapted for such uses.

It has been found that, if a substrate has a high rigidity but a large specific gravity, deflection of the disk occurs during a high-speed rotation due to its large weight with the result that vibration of the disk occurs. Conversely, if the substrate has a low specific gravity but a low rigidity, vibration of the disk likewise occurs. Accordingly, there must be a balance between apparently conflicting properties of a high rigidity and a low specific gravity. It has been found that a proper range of Young's modulus (GPa)/specific gravity is 37 or over, preferably, 39 or over, more preferably 41 or over and, most preferably, 43 or over. It has also been found that there is a preferred range of rigidity. Even if the above ratio is satisfied with a low specific gravity, Young's modulus of at least 96 GPa is preferable from the standpoint of preventing vibration of the disk. In examples of the present invention, the glass-ceramic substrate has Young's modulus of 96 GPa or over and 114 GPa or below. As to specific gravity, having regard to prevention of vibration, the substrate should preferably have specific gravity of 2.60 or below and more preferably 2.50 or below even if the substrate has a high rigidity. In examples of the present invention, the substrate has a specific gravity within a range from 2.40 to 2.60.

An information storage medium used for mobiles is required to have a shock proof property (100 G to 500 G) and a high mechanical strength in a head strap. For this reason, the substrate should preferably have bending strength of 400 MPa or over and, more preferably 500 MPa or over. In examples of the invention, the substrate has bending strength within a range from 400 MPa to 800 MPa.

Reasons for limiting the composition range of the base glass as defined in the claims will now be described.

The $SiO_2$ ingredient is a very important ingredient for growing lithium disilicate ($Li_2O \cdot 2SiO_2$), α-quartz (α-$SiO_2$), α-quartz solid solution (α-$SiO_2$ solid solution, α-cristobalite (α-$SiO_2$) and α-cristobalite solid solution (α-$SiO_2$ solid solution) as predominant crystal phases by heat treating the base glass. If the amount of this ingredient is below 70%, grown crystals of the glass-ceramic becomes instable and its texture tends to become coarse. If the amount of this ingredient exceeds 77%, difficulty arises in melting and forming of the glass.

The $Li_2O$ ingredient is a very important ingredient for growing lithium disilicate ($Li_2O \cdot 2SiO_2$) as a predominant crystal phase by heat treating the base glass. If the amount of this ingredient is below 8%, difficulty arises in growing of this crystal phase and also in melting of the base glass. If the amount of this ingredient exceeds 12%, the grown crystal is instable and its texture tends to become coarse and its chemical durability is deteriorated.

The $K_2O$ ingredient improves the melting property of the glass and prevents the grown crystal from becoming too coarse. Since an excessive amount of this ingredient causes coarseness of the grown crystal, change in the crystal phase and deterioration in chemical durability, the amount of up to 3% of this ingredient will be preferable.

The MgO and ZnO ingredients are effective for improving the melting property of the glass, preventing grown crystal grains from becoming too coarse and enabling crystal grains of lithium disilicate ($Li_2O \cdot 2SiO_2$), α-quartz (α-$SiO_2$), α-quartz solid solution (α-$SiO_2$ solid solution), α-cristobalite (α-$SiO_2$) and α-cristobalite solid solution (α-$SiO_2$ solid solution) to grow in a globular shape. For these purposes, the amount of the MgO ingredient should preferably be 0.3% or over and the amount of the ZnO ingredient should preferably be 0.1% or over. If the amounts of the MgO and ZnO ingredients are excessive, the crystal obtained will be instable and its texture will become too coarse. The amount of the MgO ingredient, therefore, should preferably be 2% or below and, more preferably, 1% or below. Likewise, the amount of the ZnO ingredient should preferably be 2% or below and, more preferably, 1% or below. The total amount of the MgO and ZnO ingredients should preferably be 2% or below, preferably 1% or below.

The $P_2O_5$ ingredient is indispensable as a nucleating agent. For enhancing forming of nucleus and preventing grown crystal grains from becoming too coarse, the amount of this ingredient should preferably be 1.5% or over. For preventing opaque devitrification of the base glass and maintaining stable large scale production, the amount of this ingredient should preferably be 3% or below.

The $ZrO_2$ ingredient is an important ingredient which, in addition to the functions, like the $P_2O_5$ ingredient, as a nucleating agent, is effective for making the grown crystals fine, improving the mechanical strength and improving chemical durability. For achieving these effects, a preferable amount of the $ZrO_2$ ingredient is 2% or over. If an excessive amount of the $ZrO_2$ ingredient is added, difficulty arises in melting of the base glass and $ZrSiO_4$ and the like slug are left unmelted, so that a preferable amount of the $ZrO_2$ ingredient is 7% or below.

The $Al_2O_3$ ingredient is effective for improving chemical durability and mechanical strength, particularly hardness, of the glass-ceramic. A preferable amount of this ingredient is 3% or over and, more preferably, 4% or over. If an excessive amount of the $Al_2O_3$ ingredient is added, the grown crystal phase changes to β-spodumene ($Li_2O \cdot Al_2O_3 \cdot 4SiO_2$). Since growth of β-spodumene and β-cristobalite significantly decreases the coefficient of thermal expansion of the material, growth of such crystal should be avoided. For this purpose, a preferable range of this ingredient is 9% or below and, more preferably, 8% or below.

The $Sb_2O_3$ and $As_2O_3$ ingredients may be added as a refining agent in melting the base glass. Addition of these ingredients in the total amount up to 2% and, preferably up to 1%, will suffice.

Reasons why the substrate does not substantially contain $Na_2O$ and PbO will now be described. $Na_2O$ in a material causes problems in producing a high precision and fine-grained magnetic film. If the substrate contains this ingredient, diffusion of Na ion into the magnetic film occurs during the film forming process and this makes the magnetic film grains to become coarse and deteriorates orientation with resulting deterioration in the magnetic property. Further, the diffusion of the Na ion into the magnetic film adversely affects a long-term stability of the magnetic property. The substrate should also be free of PbO which is undesirable from the standpoint of environment protection.

For manufacturing the glass-ceramic substrate for an information storage medium according to the invention, glass materials of the above-described composition are melted and are subjected to a hot or cold forming process. The formed glass is subjected to heat treatment under a temperature within a range from 500° C. to 600° C. for one to seven hours for nucleation and then is subjected to further heat treatment under a temperature within a range from 700° C. to 780° C. for one to twelve hours for crystallization.

The glass-ceramic thus obtained by the above heat treatment contains, as a predominant crystal phase or phases, lithium disilicate ($Li_2O \cdot 2SiO_2$) or a combination of lithium disilicate and at least one crystal selected from the group consisting of α-quartz (α-SiO$_2$), α-quartz solid solution (α-SiO$_2$ solid solution), α-cristobalite (α-SiO$_2$) and α-cristobalite solid solution (α-SiO$_2$ solid solution. The degree of crystallization of lithium disilicate is within a range from 3% to 20% and its crystal grain diameter is within a range from 0.005 μm and 0.05 μm. The degree of crystallization of α-quartz and α-quartz solid solution is within a range from 5% to 25% and their crystal grain diameter is within a range from 0.01 μm to 0.10 μm. The degree of crystallization of α-cristobalite and α-cristobalite solid solution is within a range from 2% to 10% and their crystal grain diameter is within a range from 0.01 μm to 0.10 μm.

The glass-ceramic subsequently is lapped and polished in a conventional manner to provide a glass-ceramic substrate for an information storage medium having a surface roughness Ra (arithmetic mean roughness) within a range from 1.0 Å to 5.0 Å. An information storage disk is obtained by forming a magnetic film and, if necessary, other layers including Ni—P plating, an undercoat layer, a protective layer and a lubricating layer, on the glass-ceramic substrate.

EXAMPLES

Examples of the present invention will now be described.

Tables 1 to 5 show examples (No. 1 to No. 25) of compositions of the glass-ceramic substrate for an information storage medium made according to the invention together with the temperature of nucleation, temperature of crystallization, predominant crystal phases, crystal grain diameter (average), degree of crystallization, a coefficient of thermal expansion, Young's modulus (GPa), specific gravity, Young's modulus (GPa)/specific gravity, bending strength and surface roughness Ra (arithmetic mean roughness) after polishing. Table 6 shows compositions and the above properties of the prior art Li$_2$O—SiO$_2$ system glass-ceramics disclosed in Japanese Patent Application Laid-open Publication Sho 62-72547 (Comparative Example 1) and Japanese Patent Application Laid-open Publication Hei 9-35234 (Comparative Example 2). In Tables 1 to 6, lithium disilicate is abbreviated as "LD", α-quartz as "α-q" and α-cristobalite as "α-c" respectively.

TABLE 1

| Ingredients (weight %) | Examples | | | | |
|---|---|---|---|---|---|
| | 1 | 2 | 3 | 4 | 5 |
| SiO$_2$ | 75.3 | 75.3 | 75.3 | 75.0 | 75.0 |
| Li$_2$O | 9.9 | 9.9 | 9.9 | 9.9 | 9.5 |
| P$_2$O$_5$ | 2.0 | 2.0 | 2.0 | 2.0 | 2.5 |
| ZrO$_2$ | 2.3 | 2.3 | 2.3 | 3.0 | 3.9 |
| Al$_2$O$_3$ | 7.0 | 7.0 | 7.0 | 7.0 | 7.0 |
| MgO | 0.8 | 0.8 | 0.8 | 0.4 | 0.0 |
| ZnO | 0.5 | 0.5 | 0.5 | 0.5 | 0.5 |
| K$_2$O | 2.0 | 2.0 | 2.0 | 2.0 | 1.4 |
| Sb$_2$O$_3$ | 0.2 | 0.2 | 0.2 | 0.2 | 0.2 |
| As$_2$O$_3$ | 0.0 | 0.0 | 0.0 | 0.0 | 0.0 |
| PbO | | | | | |
| Nucleation temperature (° C.) | 540 | 540 | 540 | 520 | 540 |
| Nucleation time (hour) | 5 | 7 | 5 | 5 | 2 |
| Crystallization temperature (° C.) | 720 | 740 | 760 | 730 | 740 |
| Crystallization time (hour) | 3 | 4 | 3 | 6 | 4 |
| Predominant crystal phase | | | | | |
| | LD | LD | LD | LD | LD |
| Grain diameter (average, μm) | 0.005 | 0.005 | 0.020 | 0.010 | 0.020 |
| Degree of crystallization (%) | 8 | 10 | 18 | 5 | 7 |
| | — | α-q | α-q | α-q | — |

TABLE 1-continued

| Ingredients (weight %) | Examples | | | | |
|---|---|---|---|---|---|
| | 1 | 2 | 3 | 4 | 5 |
| Grain diameter (average, μm) | — | 0.010 | 0.030 | 0.010 | — |
| Degree of crystallization (%) | — | 16 | 25 | 5 | — |
| | — | — | — | — | α-c |
| Grain diameter (average, μm) | — | — | — | — | 0.010 |
| Degree of crystallization (%) | — | — | — | — | 7 |
| Coefficient of thermal expansion (×10$^{-7}$/° C.) (−50° C.−+70° C.) | 65 | 74 | 110 | 72 | 74 |
| Young's modulus (GPa) | 108 | 114 | 110 | 105 | 100 |
| Specific gravity | 2.45 | 2.46 | 2.47 | 2.46 | 2.47 |
| Young's modulus (GPa)/specific gravity | 44.1 | 46.3 | 44.5 | 42.7 | 40.5 |
| Bending strength (MPa) | 580 | 700 | 650 | 460 | 760 |
| Surface roughness (Ra) (Å) | 1.0 | 1.2 | 2.0 | 1.1 | 1.7 |

TABLE 2

| Ingredients (weight %) | Examples | | | | |
|---|---|---|---|---|---|
| | 6 | 7 | 8 | 9 | 10 |
| SiO$_2$ | 76.0 | 76.0 | 70.5 | 76.7 | 76.5 |
| Li$_2$O | 9.5 | 10.0 | 11.5 | 8.5 | 8.3 |
| P$_2$O$_5$ | 2.3 | 2.5 | 1.7 | 1.8 | 1.8 |
| ZrO$_2$ | 4.5 | 3.0 | 6.0 | 5.0 | 2.5 |
| Al$_2$O$_3$ | 6.0 | 4.5 | 8.0 | 4.5 | 7.4 |
| MgO | 0.0 | 0.9 | 0.3 | 0.5 | 0.5 |
| ZnO | 0.0 | 0.4 | 0.3 | 0.5 | 1.5 |
| K$_2$O | 1.5 | 2.5 | 1.5 | 2.0 | 1.3 |
| Sb$_2$O$_3$ | 0.2 | 0.2 | 0.0 | 0.5 | 0.2 |
| As$_2$O$_3$ | 0.0 | 0.0 | 0.2 | 0.0 | 0.0 |
| PbO | | | | | |
| Nucleation temperature (° C.) | 540 | 560 | 510 | 590 | 570 |
| Nucleation time (hour) | 3 | 4 | 3 | 2 | 3 |
| Crystallization temperature (° C.) | 780 | 750 | 710 | 740 | 750 |
| Crystallization time (hour) | 2 | 4 | 10 | 3 | 3 |
| Predominant crystal phase | | | | | |
| | LD | LD | LD | LD | LD |
| Grain diameter (average, μm) | 0.040 | 0.040 | 0.004 | 0.050 | 0.040 |
| Degree of crystallization (%) | 18 | 8 | 12 | 10 | 6 |
| | α-q | α-q | — | α-q | α-q |
| Grain diameter (average, μm) | 0.100 | 0.040 | — | 0.010 | 0.060 |
| Degree of crystallization (%) | 23 | 16 | — | 10 | 6 |
| | α-c | — | α-c | α-c | — |
| Grain diameter (average, μm) | 0.050 | — | 0.040 | 0.020 | — |
| Degree of crystallization (%) | 9 | — | 3 | 10 | — |
| Coefficient of thermal expansion (×10$^{-7}$/° C.) (−50° C.−+70° C.) | 79 | 75 | 66 | 120 | 69 |
| Young's modulus (GPa) | 97 | 108 | 110 | 98 | 109 |
| Specific gravity | 2.50 | 2.48 | 2.41 | 2.47 | 2.43 |
| Young's modulus (GPa)/specific gravity | 38.8 | 43.5 | 45.6 | 39.7 | 44.9 |
| Bending strength (MPa) | 580 | 780 | 610 | 500 | 600 |
| Surface roughness (Ra) (Å) | 2.9 | 2.1 | 1.7 | 4.8 | 2.5 |

TABLE 3

| Ingredients (weight %) | Examples | | | | |
|---|---|---|---|---|---|
| | 16 | 17 | 18 | 19 | 20 |
| SiO$_2$ | 73.0 | 75.5 | 74.2 | 71.0 | 72.6 |
| Li$_2$O | 8.8 | 8.5 | 9.0 | 10.0 | 11.0 |
| P$_2$O$_5$ | 1.7 | 1.7 | 1.8 | 2.0 | 2.0 |
| ZrO$_2$ | 5.0 | 4.0 | 3.0 | 6.5 | 5.3 |
| Al$_2$O$_3$ | 8.4 | 3.8 | 7.8 | 3.5 | 3.8 |
| MgO | 0.0 | 2.0 | 1.7 | 1.1 | 1.0 |
| ZnO | 0.3 | 1.5 | 0.0 | 2.0 | 0.5 |
| K$_2$O | 2.3 | 2.5 | 2.0 | 2.4 | 2.8 |
| Sb$_2$O$_3$ | 0.5 | 0.5 | 0.5 | 0.0 | 0.5 |

TABLE 3-continued

| Ingredients (weight %) | Examples | | | | |
|---|---|---|---|---|---|
| | 16 | 17 | 18 | 19 | 20 |
| $As_2O_3$ | 0.0 | 0.0 | 0.0 | 1.5 | 0.5 |
| PbO | | | | | |
| Nucleation temperature (° C.) | 540 | 540 | 560 | 540 | 550 |
| Nucleation time (hour) | 5 | 5 | 1 | 3 | 5 |
| Crystallization temperature (° C.) | 740 | 740 | 780 | 720 | 740 |
| Crystallization time (hour) | 3 | 3 | 1 | 6 | 5 |
| Predominant crystal phase | LD | LD | LD | LD | LD |
| Grain diameter (average, μm) | 0.030 | 0.040 | 0.030 | 0.020 | 0.020 |
| Degree of crystallization (%) | 6 | 8 | 12 | 18 | 8 |
| | α-q | α-q | α-q | α-q | α-q |
| Grain diameter (average, μm) | 0.020 | 0.090 | 0.040 | 0.030 | 0.010 |
| Degree of crystallization (%) | 5 | 5 | 6 | 5 | 10 |
| | — | α-c | — | α-c | — |
| Grain diameter (average, μm) | — | 0.050 | — | 0.020 | — |
| Degree of crystallization (%) | — | 6 | — | 3 | — |
| Coefficient of thermal expansion (×$10^{-7}$/° C.) (−50° C.→+70° C.) | 66 | 110 | 100 | 95 | 90 |
| Young's modulus (GPa) | 110 | 96 | 100 | 96 | 105 |
| Specific gravity | 2.41 | 2.44 | 2.42 | 2.44 | 2.43 |
| Young's modulus (GPa)/specific gravity | 45.6 | 39.3 | 41.3 | 39.3 | 43.2 |
| Bending strength (MPa) | 780 | 410 | 600 | 520 | 760 |
| Surface roughness (Ra) (Å) | 2.1 | 4.9 | 3.5 | 4.0 | 2.1 |

TABLE 4

| | Examples | | | | |
|---|---|---|---|---|---|
| | 16 | 17 | 18 | 19 | 20 |
| Ingredients (weight %) | | | | | |
| $SiO_2$ | 73.0 | 75.5 | 74.2 | 71.0 | 72.6 |
| $Li_2O$ | 8.8 | 8.5 | 9.0 | 10.0 | 11.0 |
| $P_2O_5$ | 1.7 | 1.7 | 1.8 | 2.0 | 2.0 |
| $ZrO_2$ | 5.0 | 4.0 | 3.0 | 6.5 | 5.3 |
| $Al_2O_3$ | 8.4 | 3.8 | 7.8 | 3.5 | 3.8 |
| MgO | 0.0 | 2.0 | 1.7 | 1.1 | 1.0 |
| ZnO | 0.3 | 1.5 | 0.0 | 2.0 | 0.5 |
| $K_2O$ | 2.3 | 2.5 | 2.0 | 2.4 | 2.8 |
| $Sb_2O_3$ | 0.5 | 0.5 | 0.5 | 0.0 | 0.5 |
| $As_2O_3$ | 0.0 | 0.0 | 0.0 | 1.5 | 0.5 |
| PbO | | | | | |
| Nucleation temperature (° C.) | 540 | 540 | 560 | 540 | 550 |
| Nucleation time (hour) | 5 | 5 | 1 | 3 | 5 |
| Crystallization temperature (° C.) | 740 | 740 | 780 | 720 | 740 |
| Crystallization time (hour) | 3 | 3 | 1 | 6 | 5 |
| Predominant crystal phase | LD | LD | LD | LD | LD |
| Grain diameter (average, μm) | 0.030 | 0.040 | 0.030 | 0.020 | 0.020 |
| Degree of crystallization (%) | 6 | 8 | 12 | 18 | 8 |
| | α-q | α-q | α-q | α-q | α-q |
| Grain diameter (average, μm) | 0.020 | 0.090 | 0.040 | 0.030 | 0.010 |
| Degree of crystallization (%) | 5 | 5 | 6 | 5 | 10 |
| | — | α-c | — | α-c | — |
| Grain diameter (average, μm) | — | 0.050 | — | 0.020 | — |
| Degree of crystallization (%) | — | 6 | — | 3 | — |
| Coefficient of thermal expansion (×$10^{-7}$/° C.) (−50° C.→+70° C.) | 66 | 110 | 100 | 95 | 90 |

TABLE 4-continued

| | Examples | | | | |
|---|---|---|---|---|---|
| | 16 | 17 | 18 | 19 | 20 |
| Young's modulus (GPa) | 110 | 96 | 100 | 96 | 105 |
| Specific gravity | 2.41 | 2.44 | 2.42 | 2.44 | 2.43 |
| Young's modulus (GPa)/specific gravity | 45.6 | 39.3 | 41.3 | 39.3 | 43.2 |
| Bending strength (MPa) | 780 | 410 | 600 | 520 | 760 |
| Surface roughness (Ra) (Å) | 2.1 | 4.9 | 3.5 | 4.0 | 2.1 |

TABLE 5

| | Examples | | | | |
|---|---|---|---|---|---|
| Ingredients (weight %) | 21 | 22 | 23 | 24 | 25 |
| $SiO_2$ | 72.0 | 76.5 | 76.5 | 73.7 | 74.4 |
| $Li_2O$ | 10.5 | 8.3 | 10.2 | 9.0 | 8.3 |
| $P_2O_5$ | 2.0 | 1.8 | 2.0 | 1.8 | 1.8 |
| $ZrO_2$ | 6.5 | 2.5 | 2.5 | 2.5 | 2.5 |
| $Al_2O_3$ | 4.0 | 5.0 | 6.0 | 8.0 | 7.0 |
| MgO | 1.1 | 0.5 | 0.5 | 0.5 | 0.5 |
| ZnO | 1.5 | 1.0 | 0.0 | 0.5 | 1.0 |
| $K_2O$ | 2.4 | 2.4 | 1.5 | 2.5 | 2.5 |
| $Sb_2O_3$ | 0.0 | 2.0 | 0.8 | 0.0 | 0.0 |
| $As_2O_3$ | 0.0 | 0.0 | 0.0 | 1.5 | 2.0 |
| PbO | | | | | |
| Nucleation temperature (° C.) | 520 | 570 | 540 | 530 | 600 |
| Nucleation time (hour) | 3 | 1 | 3 | 7 | 2 |
| Crystallization temperature (° C.) | 780 | 760 | 720 | 740 | 700 |
| Crystallization time (hour) | 1 | 2 | 8 | 3 | 10 |
| Predominant crystal phase | LD | LD | LD | LD | LD |
| Grain diameter (average, μm) | 0.050 | 0.030 | 0.010 | 0.010 | 0.005 |
| Degree of crystallization (%) | 19 | 15 | 4 | 10 | 10 |
| | α-q | α-q | α-q | α-q | — |
| Grain diameter (average, μm) | 0.030 | 0.020 | 0.010 | 0.020 | — |
| Degree of crystallization (%) | 20 | 15 | 6 | 5 | — |
| | — | — | α-c | — | α-c |
| Grain diameter (average, μm) | — | — | 0.010 | — | 0.010 |
| Degree of crystallization (%) | — | — | 5 | — | 3 |
| Coefficient of thermal expansion (×$10^{-7}$/° C.) (−50° C.→+70° C.) | 110 | 100 | 68 | 80 | 70 |
| Young's modulus (GPa) | 96 | 98 | 110 | 100 | 110 |
| Specific gravity | 2.51 | 2.44 | 2.46 | 2.43 | 2.44 |
| Young's modulus (GPa)/specific gravity | 38.2 | 40.2 | 44.7 | 41.2 | 45.1 |
| Bending strength (MPa) | 490 | 500 | 780 | 650 | 760 |
| Surface roughness (Ra) (Å) | 5.0 | 4.0 | 1.5 | 1.8 | 1.1 |

TABLE 6

| | Comparative Examples | |
|---|---|---|
| Ingredients (weight %) | 1 | 2 |
| $SiO_2$ | 74.2 | 76.1 |
| $Li_2O$ | 9.6 | 11.8 |
| $P_2O_5$ | 1.5 | 2.0 |
| $ZrO_2$ | 0.4 | |
| $Al_2O_3$ | 9.6 | 7.1 |
| MgO | | |
| ZnO | | |
| $K_2O$ | 2.4 | 2.8 |
| $Sb_2O_3$ | | 0.2 |
| $As_2O_3$ | | |
| PbO | 2.3 | |
| Nucleation temperature (° C.) | 540 | 500 |
| Nucleation time (hour) | 3 | 3 |
| Crystallization temperature (° C.) | 800 | 850 |
| Crystallization time (hour) | 2 | 3 |

TABLE 6-continued

|  | Comparative Examples | |
|---|---|---|
| Ingredients (weight %) | 1 | 2 |
| Predominant crystal phase | | |
|  | LD | LD |
| Grain diameter (average, μm) | 1.50 | 0.10 |
| Degree of crystallization (%) | 45 | 48 |
|  | — | β-spodumene |
| Grain diameter (average, μm) | — | 0.20 |
| Degree of crystallization (%) | — | 21 |
|  | α-c | — |
| Grain diameter (average, μm) | 0.300 | — |
| Degree of crystallization (%) | 16 | — |
| Coefficient of thermal expansion ($\times 10^{-7}/°$ C.) ($-50°$ C.–$+70°$ C.) | 48 | 49 |
| Young's modulus (GPa) | 86 | 82 |
| Specific gravity | 2.46 | 2.55 |
| Young's modulus (GPa)/ specific gravity | 35.0 | 32.2 |
| Bending strength (MPa) | 320 | 300 |
| Surface roughness (Ra) (Å) | 12 | 11 |

For manufacturing the glass-ceramic substrate of the above described examples, materials including oxides, carbonates and nitrates are mixed and molten in conventional melting apparatus at a temperature within the range from about 1350° C. to about 1450° C. The molten glass is stirred to homogenize it and thereafter formed into a disk shape and annealed to provide a formed glass. Then, the formed glass is subjected to heat treatment to produce the crystal nucleus under a temperature within the range from 500° C. to 600° C. for about one to seven hours and then is further subjected to heat treatment for crystallization under a temperature within the range from 700° C. to 780° C. for about one to twelve hours to obtain a desired glass-ceramic. Then, this glass-ceramic is lapped with diamond pellets of 800# to 2000# for about 5 minutes to 30 minutes and then is finally polished with a cerium oxide polishing agent having grain diameter ranging from 0.02 μm to 3 μm for about 30 minutes to 60 minutes.

The crystal grain diameters (average) of the respective crystal phases were measured by a transmission electron microscope (TEM). The types of the respective crystal grains were identified by the TEM structure analysis.

The degree of crystallization of the respective crystal types was obtained by preparing a 100% crystal reference specimen for each crystal type and measuring, with an X-ray diffractometer (XRD), the degree of crystallization of each crystal type on the basis of diffraction peak area employing the internal standard method.

The surface roughness Ra (arithmetic mean roughness) was measured with an atomic force microscope (AFM).

The bending strength was calculated by the cup type ring-bending test on the basis of the inner diameter, outer diameter, thickness, Poisson's ratio and maximum load.

Figure 1:
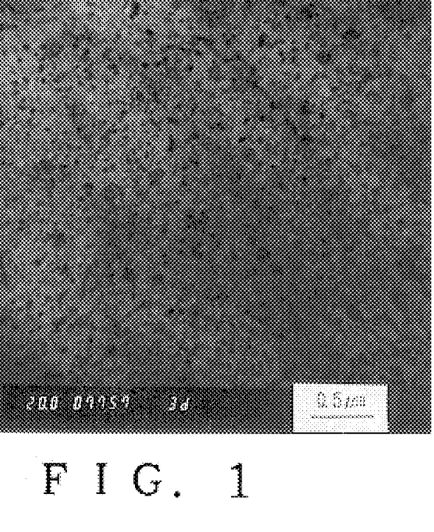
FIG. 1 is a transmission electron microscope (TEM) photograph (20,000 magnifications) of the glass-ceramic of Example 3.
Figure 2:
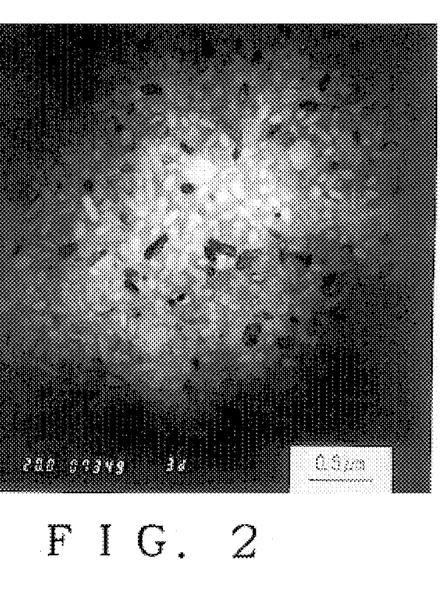
FIG. 2 is a TEM photograph (20,000 magnifications) of the glass-ceramic of Comparative Example 2.

TEM photographs showing the crystal grain shapes of Example 3 of the present invention and Comparative Example 2 are shown in FIGS. 1 and 2.

In FIG. 1, the crystal grains are all fine globular grains. The crystal grain diameter of lithium disilicate is within a range from 0.01 μm and 0.05 μm with an average crystal grain diameter of 0.02 μm. The crystal grain diameter of α-quartz is within a range from 0.02 μm to 0.05 μm with an average crystal grain diameter of 0.03 μm.

In FIG. 2, the crystal grains are all acicular or rice grain shape having a relatively large diameter. The crystal grain diameter of lithium disilicate is within a range from 0.06 μm to 0.2 μm with an average crystal grain diameter of 0.1 μm. The crystal grain diameter of β-spodumene is within a range from 0.1 μm to 0.4 μm with an average crystal grain diameter of 0.2 μm.

As shown in Tables 1 to 6 and FIGS. 1 and 2, the glass-ceramics of the present invention are different from the comparative examples of the prior art $Li_2O \cdot 2SiO_2$ system glass-ceramics in the crystal grain diameter (average) and degree of crystallization. In the glass-ceramics of the present invention, a predominant crystal phase or phases consists of lithium disilicate ($Li_2O \cdot 2SiO_2$) or a combination of lithium disilicate ($Li_2O \cdot 2SiO_2$) and at least one crystal phase selected from the group consisting of α-quartz (α-$SiO_2$), α-quartz solid solution (α-$SiO_2$ solid solution), α-cristobalite (α-$SiO_2$) and α-cristobalite solid solution (α-$SiO_2$ solid solution) and the crystal grains are fine globular grains whereas in the glass-ceramic of Comparative Example 1, the lithium disilicate crystal phase has a large grain diameter (average) of 1.5 μm or over and, in the glass-ceramic of Comparative Example 2, the β-spodumene crystal phase has also a large grain diameter (average) of 0.2 μm. The crystal grains of these comparative examples are all of an acicular or rice grain shape. In view of the current tendency toward the super flatness, the glass-ceramics of the comparative examples will cause difficulty in the surface roughness after polishing and cause other defects. The glass-ceramics of Comparative Examples 1 and 2 have surface roughness Ra of 11 Å and over which shows that it is extremely difficult in the comparative examples to obtain an excellent flat surface characteristic required.

Further, as regards the coefficient of thermal expansion, the glass-ceramics of the Comparative Examples 1 and 2 have a low coefficient of thermal expansion of $49 \times 10^{-7}/°$ C. or below which is quite unsuitable for realizing matching of the coefficient of thermal expansion between an information storage medium and a drive device. Furthermore, the glass-ceramics of Comparative Examples 1 and 2 have a low Young's modulus of 86 GPa or below and a low bending strength of 320 MPa or below.

Figure 3:
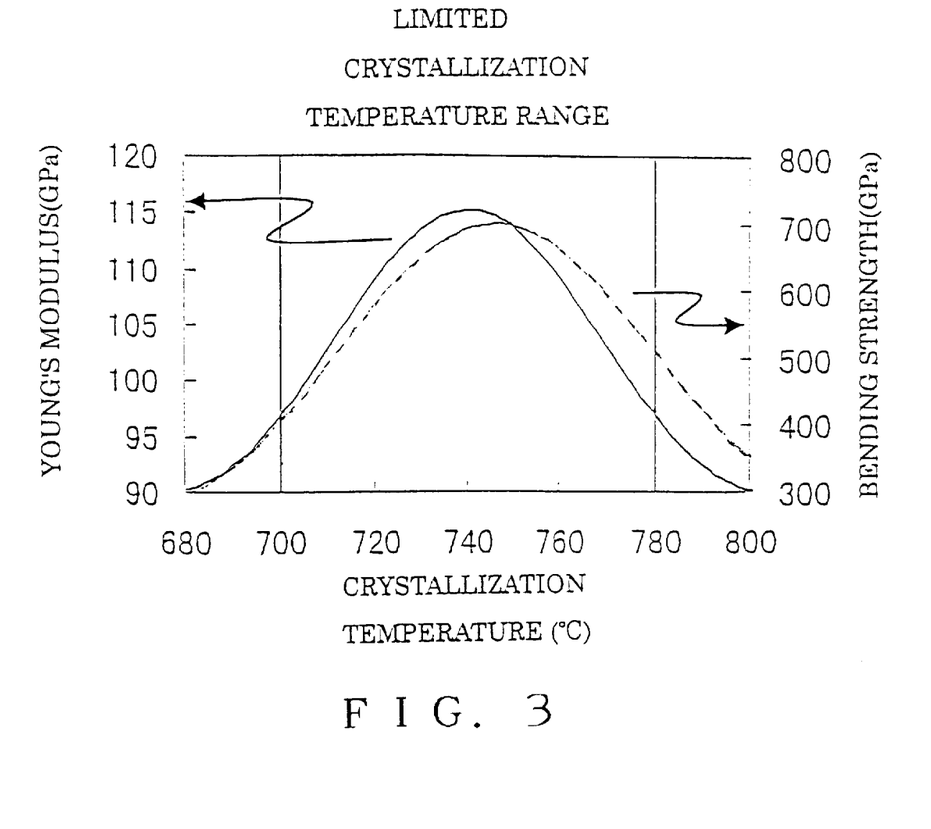
FIG. 3 is a graph showing relationship between crystallization temperature and Young's modulus and bending strength of Example 1.
Figure 4:
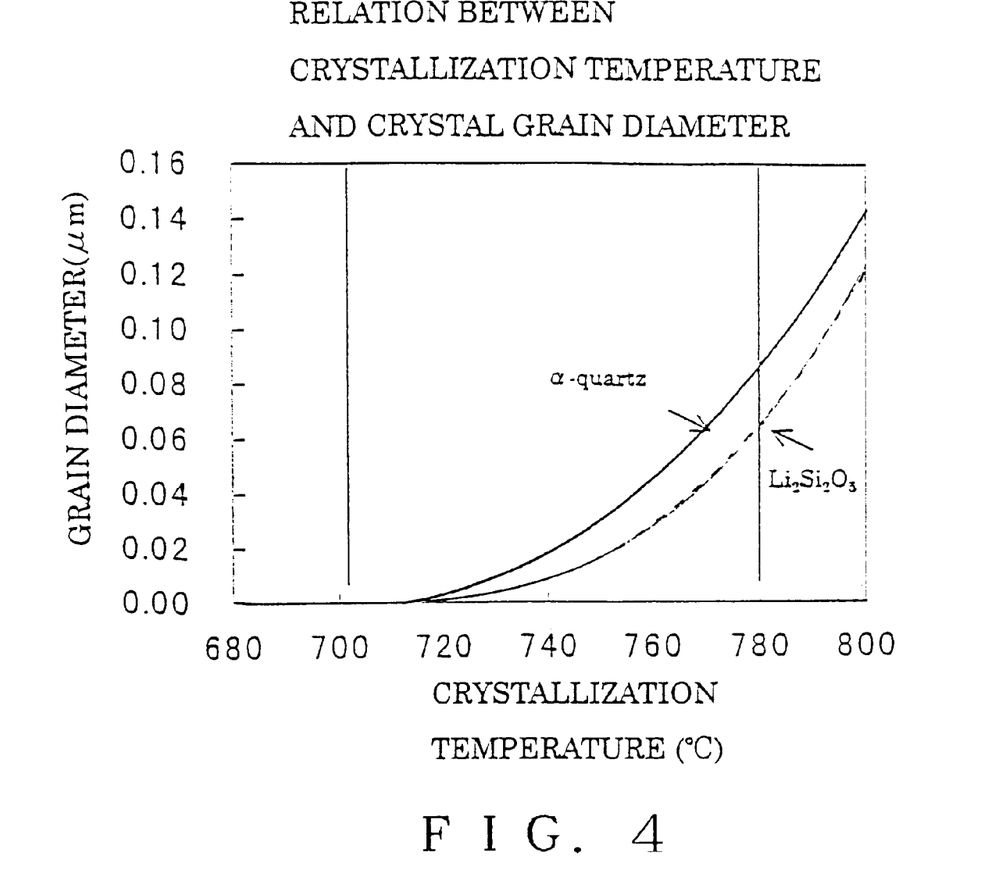
FIG. 4 is a graph showing relationship between crystallization temperature and crystal grain diameter (average) of Example 1.

Graph of FIG. 3 shows, with respect to Example 1, crystallization temperature with respect to Young's modulus and bending strength which define the present invention and graph of FIG. 4 shows, also with respect to Example 1, crystallization temperature with respect to crystal grain diameter which define the present invention. As shown in FIGS. 3 and 4, it will be apparent that the crystallization temperature exerts a great influence to the crystal grain diameter, Young's modulus and bending strength and this constitutes the basis on which the limited values in the claims are defined.

On the glass-ceramic substrates of the above described examples are formed films of a Cr middle layer (80 nm), a Co—Cr magnetic layer (50 nm) and a SiC protective layer (10 nm) by the DC sputtering method. Then, a perfluoropolyether lubricant (5 nm) is coated over the formed film to provide an information storage medium. The information storage medium thus obtained can reduce the glide height as compared to the prior art information storage medium owing to its excellent super flatness. Further, the information storage medium of the invention can be used for the information storage device of the ramp loading system in which the magnetic head performs inputting and outputting of signals in contact with the surface of the information storage medium without damaging the head or medium. Furthermore, the information storage medium of the invention can provide a stable surface contour also by laser texturing used for the landing zone system.

As described above, according to the present invention, there is provided a glass-ceramic substrate suitable for an information storage medium which has eliminated the disadvantages of the prior art substrates and has a flat surface characteristic capable of coping with a low glide height or contact recording of a magnetic head necessitated by a high recording density, has a high Young's modulus and a low specific gravity suitable for a high-speed rotation necessitated by a high-speed transfer of information, and has mechanical strength which is indispensable for uses for mobiles. According to the invention, there are also provided a method for manufacturing the glass-ceramic substrate and an information storage medium using this substrate.

What is claimed is:

1. A glass-ceramic substrate for an information storage medium comprising, as a predominant crystal phase, lithium disilicate ($Li_2O \cdot 2SiO_2$) having a crystal grain diameter (average) of 0.05 μm or below.

2. A glass-ceramic substrate as defined in claim 1 wherein Young's modulus (GPa)/specific gravity is 37 or over.

3. A glass-ceramic substrate consisting of a crystal phase or phases and an amorphous phase and having a crystal grain diameter (average) of 0.05 μm or below and comprising $SiO_2$ in the amount of 70–77% and $Li_2O$ in the amount of 8–12% wherein Young's modulus (Gpa)/specific gravity is 37 or over.

4. A glass-ceramic substrate as defined in claim 1 wherein the degree of crystallization of the lithium disilicate crystal phase is within a range of 3% to 20% crystallinity.

5. A glass-ceramic substrate as defined in claim 1 comprising further at least one crystal phase selected from the group consisting of α-quartz (α-$SiO_2$), α-quartz solid solution (α-$SiO_2$ solid solution), degree of crystallization of the α-quartz (α-$SiO_2$) and the α-quartz solid solution (α-$SiO_2$ solid solution) being within a range of from 5% to 25% crystallinity and a crystal grain diameter thereof (average) being 10 μm or below.

6. A glass-ceramic substrate as defined in claim 1 comprising further at least one crystal phase selected from the group consisting of α-cristobalite (α-$SiO_2$), α-cristobalite solid solution (α-$SiO_2$ solid solution), degree of crystallization of the α-cristobalite (α-$SiO_2$) and the α-cristobalite solid solution (α-$SiO_2$ solid solution) being within a range of from 2% to 10% crystallinity and a crystal grain diameter thereof (average) being 10 μm or below.

7. A glass-ceramic substrate as defined in claim 1 comprising, as predominant crystal phases, lithium disilicate ($Li_2O \cdot 2SiO_2$) and at least one crystal phase selected from the group consisting of α-quartz (α-$SiO_2$), α-quartz solid solution (α-$SiO_2$ solid solution), α-cristobalite (α-$SiO_2$) and α-cristobalite solid solution (α-$SiO_2$ solid solution).

8. A glass-ceramic as defined in claim 1 wherein crystal grains of the lithium disilicate are fine and substantially of a globular shape.

9. A glass-ceramic substrate as defined in claim 1 which is substantially free of $Na_2O$ and PbO.

10. A glass-ceramic substrate as defined in claim 1 which has a surface roughness Ra (arithmetic mean roughness) after polishing of 5.0 Å or below.

11. A glass-ceramic substrate as defined in claim 1 which has a coefficient of thermal expansion within a range from $+65 \times 1^{-7}/°$ C. to $+130 \times 10^{-7}/°$ C in a temperature range from $-50°$ C. to $+70°$ C.

12. A glass-ceramic substrate as defined in claim 1 which has bending strength of 400 MPa or over.

13. A glass-ceramic substrate as defined in claim 1 having a composition which consists in weight percent of:

| | |
|---|---|
| $SiO_2$ | 70–77% |
| $Li_2O$ | 8–12% |
| $K_2O$ | 1–3% |
| MgO | 0–2% |
| ZnO | 0–2% |
| $P_2O_5$ | 1.5–3% |
| $ZrO_2$ | 2–7% |
| $Al_2O_3$ | 3–9% |
| $Sb_2O_3 + As_2O_3$ | 0–2%. |

14. A method for manufacturing a glass-ceramic substrate for an information storage medium as defined in claim 1 which comprises steps of heat treating a base glass for nucleation under a temperature within a range from 500° C. to 600° C. for one to seven hours and further heat treating the glass for crystallization under a temperature within a range from 700° C. to 780° C. for one to twelve hours and thereafter polishing the glass-ceramic to a surface roughness Ra (arithmetic mean roughness) of 5° C. or below.

15. An information storage disk provided by forming a magnetic film and other layers including Ni—P plating, an undercoat layer, a protective layer and a lubricating layer, on a glass-ceramic substrate as defined in claim 1.

* * * * *

UNITED STATES PATENT AND TRADEMARK OFFICE
CERTIFICATE OF CORRECTION

PATENT NO. : 6,174,827 B1 Page 1 of 1
DATED : January 16, 2001
INVENTOR(S) : Naoyuki Goto et al.

It is certified that error appears in the above-identified patent and that said Letters Patent is hereby corrected as shown below:

Column 1,
Lines 37 and 45, "10." should be -- 0.10 --

Column 2,
Line 51, "5ºC" should be -- 5Å --

Signed and Sealed this

Seventeenth Day of August, 2004

JON W. DUDAS
*Acting Director of the United States Patent and Trademark Office*